(12) United States Patent
Hood et al.

(10) Patent No.: US 9,856,532 B2
(45) Date of Patent: *Jan. 2, 2018

(54) MARKERS AND METHODS FOR DETECTING POSTTRAUMATIC STRESS DISORDER (PTSD)

(71) Applicant: Institute for Systems Biology, Seattle, WA (US)

(72) Inventors: Leroy Hood, Seattle, WA (US); Kai Wang, Bellevue, WA (US); Inyoul Lee, Seattle, WA (US); Yong Zhou, Seattle, WA (US); Ji Hoon Cho, Seattle, WA (US); Dhimankrishna Ghosh, Seattle, WA (US)

(73) Assignee: INSTITUTE FOR SYSTEMS BIOLOGY, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/830,326

(22) Filed: Mar. 14, 2013

(65) Prior Publication Data

US 2014/0073516 A1 Mar. 13, 2014

Related U.S. Application Data

(60) Provisional application No. 61/698,405, filed on Sep. 7, 2012, provisional application No. 61/723,268, filed on Nov. 6, 2012.

(51) Int. Cl.
*C12Q 1/68* (2006.01)
*C40B 30/04* (2006.01)
*C40B 40/00* (2006.01)
*C40B 40/06* (2006.01)

(52) U.S. Cl.
CPC ......... *C12Q 1/6881* (2013.01); *C12Q 1/6883* (2013.01); *C12Q 2600/158* (2013.01); *C12Q 2600/178* (2013.01)

(58) Field of Classification Search
CPC .................................................... C12Q 1/68
USPC ................................................ 506/9
See application file for complete search history.

(56) References Cited

U.S. PATENT DOCUMENTS

| | | | | |
|---|---|---|---|---|
| 7,341,552 B2* | 3/2008 | Zhang | .................. | C12Q 1/6883 435/6.18 |
| 8,143,002 B2* | 3/2012 | Keene et al. | .................. | 435/6.1 |
| 2007/0099209 A1 | 5/2007 | Clarke | | |
| 2011/0212849 A1* | 9/2011 | Verweij | ........................... | 506/9 |
| 2012/0039812 A1 | 2/2012 | Holsboer et al. | | |
| 2012/0309645 A1* | 12/2012 | Keller | .................. | C12Q 1/6886 506/9 |
| 2013/0040833 A1* | 2/2013 | Noerholm et al. | ................ | 506/9 |

FOREIGN PATENT DOCUMENTS

| | | | | | |
|---|---|---|---|---|---|
| NL | WO 2011027312 | A1 | * | 3/2011 | ....... G01N 33/57484 |
| WO | WO 2006013561 | A2 | * | 2/2006 | |
| WO | WO-2010/029176 | | | 3/2010 | |
| WO | WO 2011032155 | A2 | * | 3/2011 | |
| WO | WO 2011068839 | A1 | * | 6/2011 | |
| WO | WO 2011142827 | A2 | * | 11/2011 | |
| WO | WO 2012012051 | A2 | * | 1/2012 | |
| WO | WO-2012/034189 | | | 3/2012 | |

OTHER PUBLICATIONS

Wong et al., Review Real-Time PCR for mRNA Quantitation, BioTechniques, 2005, 39(1), 75-85.*
Brock et al., Naturally Occurring Adenines Within mRNA Coding Sequences Affect Ribosome Binding and Expression in *Escherichia coli*, J. Bacteriology, 2007, 189(2), 501-510.*
Pilobello et al., Development of a Lectin Microarray for the Rapid Analysis of Protein Glycopatterns, ChemBioChem, 2005, 6, 1-4.*
Boyerinas et al., Focus Review, The Role of Let-7 in Cell Differentiation and Cancer, Endocrine-Related Cancer, 2010, 17, F19-F36.*
National Institutes of Health, The Human Genome Project Completion: Frequently Asked Questions, Department of Health and Human Services, 2010, 1-3.*
Ley et al., Reviews, New Tools and Concepts for Modern Organic Synthesis, Nature Reviews, 2002, 1, 573-586.*
Pritchard et al., Reviews, MicroRNA Profiling: Approaches and Considerations, Nature Reviews, Genetics, 2012, 13, 358-369.*
Organ et al., Optimizing Solution-Phase Synthesis Using Solid-Phase Techniques, Chapter 15, Optimization of Solid-Phase Combinatorial Synthesis, Yan and Czarnik eds., 2002, 315-318.*
Saper, C., A Guide to the Perplexed on the Specificity of Antibodies, Journal of Histochemistry & Cytochemistry, 2009, 57(1), 1-5.*
Ladd, J., Development of Surface Chemistries and Protein Arrays for Surface Plasmon Resonance Sensing in Complex Media, Dissertation, University of Washington, 2008, 1-137.*
International Search Report and Written Opinion for PCT/US2013/058608, dated Jan. 17, 2014, 14 pages.
Grover et al., "MicroRNA signature in a mouse model of post-traumatic stress disorder," Abstracts of the Annual Meeting of the Society for Neuroscience, Society for Neuroscience, Washington D.C. (2011) vol. 41, Program No. 561.25, Poster No. P5 (2 pages).
Invitation to Pay Fees and Partial International Search Report for PCT/US2013/058608, dated Nov. 8, 2013, 4 pages.
Malan-Muller et al., "Big effects of small RNAs: a review of microRNAs in anxiety," Mol Neurobiol (2013) 47(2):726-739.
Rinaldi et al., "Stress induces region specific alterations in microRNAs expression in mice," Behav Brain Res (2010) 208(1):265-269.

(Continued)

*Primary Examiner* — Amy M Bunker
(74) *Attorney, Agent, or Firm* — Morrison & Foerster LLP

(57) ABSTRACT

Concentrations of certain miRNA, mRNA and/or protein markers in the biological fluids and/or tissues of a subject are used to determine the probability that the subject does or does not have Posttraumatic Stress Disorder (PTSD). The concentrations of these markers in fluids and/or tissues are different in subjects with PTSD as compared to subjects who do not suffer from this disorder.

3 Claims, 6 Drawing Sheets

(56) References Cited

OTHER PUBLICATIONS

Uddin et al., "Gene expression and methylation signatures of MAN2C1 are associated with PTSD," (2011) 30(2-3):111-121.
Yehuda et al., "Gene expression patterns associated with post-traumatic stress disorder following exposure to the World Trade Center attacks," Biol Psychiatry (2009) 66(7):708-711.
Zhou et al., "Role of novel microRNAs in immunological dysfunction associated with PTSD," J Immunol (2011) 186:117.13.
Zieker et al., "Differential gene expression in peripheral blood of patients suffering from post-traumatic stress disorder," Mol Psychiatry (2007) 12(2):116-118.

* cited by examiner

MARKERS AND METHODS FOR DETECTING POSTTRAUMATIC STRESS DISORDER (PTSD)

CROSS-REFERENCE TO RELATED APPLICATIONS

This application claims priority from U.S. provisional application 61/698,405 filed 7 Sep. 2012 and U.S. provisional application 61/723,268 filed 6 Nov. 2012. The contents of this document are incorporated herein by reference.

STATEMENT OF RIGHTS TO INVENTIONS MADE UNDER FEDERALLY SPONSORED RESEARCH

This work was supported in part by a research contract from the Department of Defense. The U.S. government has certain rights in this invention.

TECHNICAL FIELD

The invention relates to the field of biological markers for physiological conditions. More specifically, it relates to markers for Posttraumatic Stress Disorder (PTSD) and methods to detect this disorder in subjects using these markers. The markers include microRNA, mRNA and protein circulating in body fluids.

BACKGROUND ART

Diagnosis of Posttraumatic Stress Disorder (PTSD) has been focused on phenomenological indicators such as reports of panic attacks, nightmares, disability in functioning, and other measures that focus on symptomology. To applicants' knowledge, no metabolic or physiological changes in the molecules present in biological fluids or tissues of the subject have been employed for this purpose. The present invention has identified markers that circulate in biological fluids of a subject afflicted with PTSD that change in concentration or level in comparison to subjects that are not afflicted with this disorder.

DISCLOSURE OF THE INVENTION

It has now been found that there is a multiplicity of markers whose concentration or level is different in tissues and/or bodily fluids of individuals afflicted with PTSD in comparison with individuals not so afflicted. These markers include specific microRNAs, messenger RNAs, and/or proteins. Differences in messenger RNA concentration reflect differences in gene expression, while differences in protein levels reflect combinations of gene expression differences and, in the case of fluids, propensity for secretion. MicroRNAs have been implicated in intracellular signaling and represent a potentially independent source of information regarding this condition.

Thus, in one aspect, the invention is directed to a method to evaluate the probability that a test subject is afflicted with Posttraumatic Stress Disorder (PTSD), which method comprises: assessing the level of at least one specific microRNA (miRNA) marker and/or at least one specific messenger RNA (mRNA) marker and/or at least one specific protein marker in a sample of cells and/or fluid from said subject and comparing the level of at least one microRNA and/or mRNA and/or protein with the level associated with corresponding cells and/or fluid from control subjects who are free of PTSD, wherein a difference in the level of said one or more miRNA and/or mRNA and/or protein in said test subject as compared to control subjects indicates a probability that said test subject is afflicted with PTSD. "Corresponding" cells and/or fluid refers to the use of the same type of sample in test subjects and controls—e.g., blood in both cases or liver cells in both cases.

In some embodiments, the level only one miRNA or mRNA or protein is measured and compared, but employing larger numbers of markers is preferred. In some embodiments, said method simultaneously determines combinations or subcombinations of said miRNA, mRNA and protein marker levels.

The inventors have identified specific markers useful in the foregoing methods. Thus, in another aspect, the invention is directed to a panel for determining the probability of the presence or absence of PTSD in a subject wherein said panel contains detection reagents for at least two microRNA selected from the group consisting of has-let-7a, hsa-let-7a*, hsa-miR-16, hsa-miR-33b, hsa-miR-146a, hsa-miR-185, hsa-miR-185*, hsa-miR-188-5p, hsa-miR-188-3p, hsa-miR-210, hsa-miR-505, hsa-miR-551, hsa-miR-598 and hsa-miR-663; and/or wherein said panel contains detection reagents for at least two mRNA selected from the group consisting of HGD, RGS18, ND1, NT5C3, IGF2BP3, NEXN, HEXM2, DAPP1, SAV1, ID4, CXCR5, HS3ST1, CD72, TLR10, BANK1, MS4A1, FCRLA, CD79B, PPAPDC1B, TLC1A, KCNG1, FCRL1, FCRL2, BCOR, TC2N, LYPLAL1, RPA1, HMBOX1, RAMP1, FCGR1B, ADM, PRDM1, B4GALT5, MXRA7, TXNDC5, IGJ and LOC729451; and/or wherein said panel contains detection reagents for at least two proteins selected from the group consisting of ANK3, APOD, BSN, CNP, CACNA1B, CNTN1, CNTN2, CRH, DCLK1, ELAVL3, ENC1, FSD1, FOXG1, GNAO1, GRIA1, GRIA2, GRIA3, GRIN1, GRM7, KCNC1, LGI1, LRRTM4, MAG, MAP3K12, MBP, NAP1L5, NCAM2, OLFM1, OLFM3, PRKAR1B, RASGRF1, RPH3A, SCG3, SNAP25, SST, STMN2, SYN1 and UCHL1, or the panel may include only one representative from at least two of the categories listed.

In an important aspect, the invention relates to panels that have representatives of more than one type of marker. In particular, the panel may contain a detection reagent for a protein, especially PRKAR1B or protein B along with at least one detection reagent for microRNA or messenger RNA.

Thus, in another aspect, the invention is directed to panels and methods that employ detection reagents for PRKAR1B along with a detection reagent for a microRNA and/or a detection reagent for a messenger RNA.

The invention also relates to kits containing one or more of the foregoing panels, including one or any combination of two such panels or all three in the same kit.

In still another aspect, the invention is directed to specific methods for measuring simultaneously in the same sample markers of different chemical natures, such as proteins, mRNA, miRNA, DNA and the like.

MODES OF CARRYING OUT THE INVENTION

Figure 1:
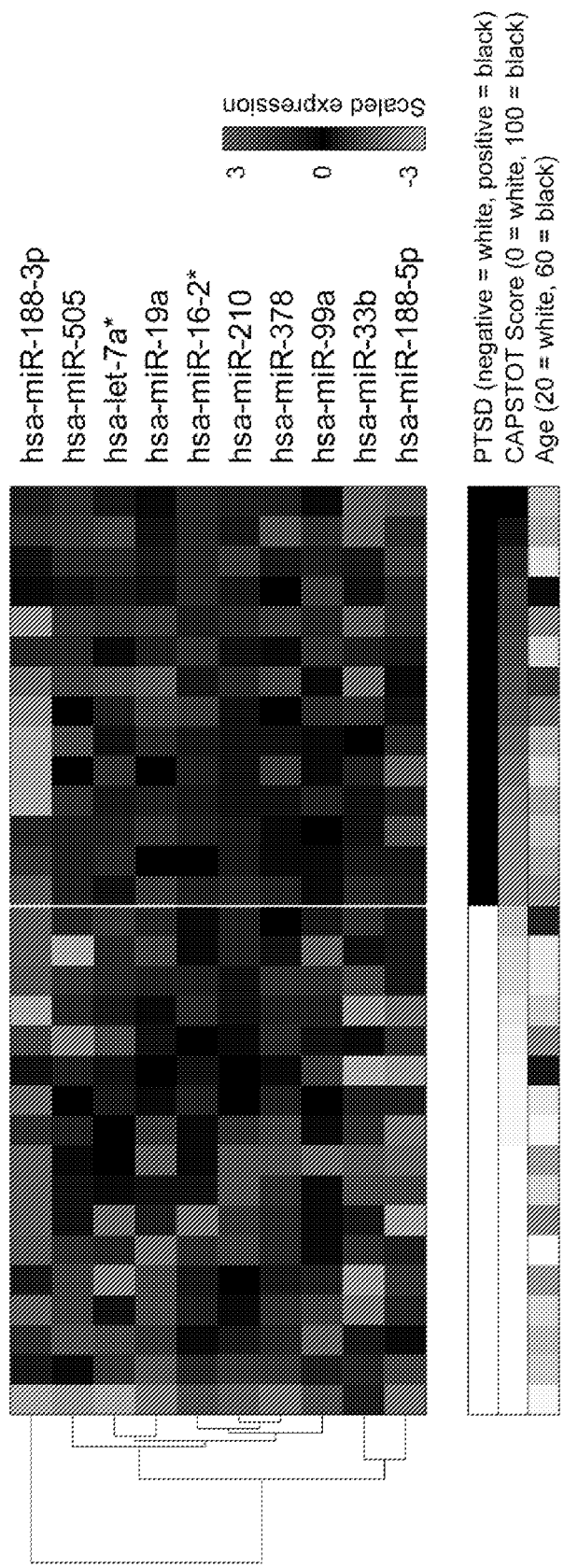
FIG. 1 shows the expression pattern of 10 microRNA markers in human plasma samples separating PTSD positive samples from PTSD negative.

A multiplicity of markers has been identified whose levels in biological fluids are different in PTSD positive subjects as opposed to subjects that are free of PTSD by conventional diagnosis. Markers can be assessed in biological fluids of humans or other test subjects including blood and fractions thereof, lymph, cerebrospinal fluid, saliva, urine, semen, and any other exudates. The levels of markers may also be measured in tissues, however the use of biological fluids is more convenient. Further, since the level of these markers in tissues and fluids may not vary concomitantly with the presence or absence of PTSD, standardization of marker choice with respect to the nature of the biological sample is desirable. That is, the corresponding fluids or tissues should be used in test subjects and controls.

While measurement of a single marker is useful, the use of a multiplicity of such markers sometimes improves the probability that the diagnosis is accurate. Nevertheless, the results obtained indicate that in some cases the measurement of only one marker results in assessments with acceptable specificities and sensitivities. Use of two, three, four, five, seven, ten or more markers is also within the scope of the invention, and in most cases the larger the number of markers, the higher the probability that the diagnosis is correct. As the foregoing implies, it is possible to measure only, for example, microRNA or only messenger RNA or only protein, but it is also within the scope of the invention to measure combinations of these markers—i.e., representative one or more markers from the microRNA category and one or more markers from the messenger RNA category, a combination of one or more markers from the microRNA category and one or more markers from the protein category or from the messenger RNA category or from all three categories. A single biological fluid type may be used, or combinations of results from more than one type of fluid, such as lymph plus cerebrospinal fluid or blood plus saliva.

Thus, typically, the methods of the invention will employ "panels" of detection reagents for the particular markers to be assayed where, in some cases, a "panel" of only one or two detection reagents may be used or panels that contain three or many more.

As implied above, "panel" typically refers to a collection of two or more detection reagents for any combination of miRNA, and/or messenger RNA, and/or protein. However, in some cases, where the reagents are configured specifically for conducting the assays, the panel may include only one member. Any of the invention panels can be configured specifically for the assay, for example, by binding the reagents to a solid substrate, such as latex or magnetic beads or in an organized array on a support. The assays may, however, also be run in solution or homogeneous phase.

The nature of the detection reagents will depend on the particular assay method selected. "Detection reagents" refers to members of a panel which are able to interact selectively with the protein, mRNA or miRNA to be assessed. Typically, a detection reagent will include a binding function that is specific for the analyte to be assessed. However, other forms of selectively identifying and assessing the level of analytes are not excluded. For example, if the analyte is a protein with enzymatic activity, the detection reagent may be a substrate for the enzyme, perhaps labeled to indicate whether the enzyme has acted on it or not. If the analyte is a nucleic acid, a restriction enzyme limited by the specific sequence might be used for detection. However, the most readily envisioned detection reagents will at least include a binding function wherein the reagent is a specific binding protein for the analyte. Typically, additional reagents will be necessary to ascertain the concentration or level of the analyte/marker. (In the present application, "concentration" and "level" are used interchangeably.) For example, for detection of proteins, the panel may comprise antibodies or fragments thereof or aptamers that are specific for each of the protein markers to be detected, and an additional reagent, such as a fluorescent or radioisotope label may be needed to measure the quantity of protein captured by the binding partner.

More recently, a capture agent for proteins based on "in situ click chemistry" has been described by Millward, S. W., et al., *J. Am. Chem. Soc.* (2001) 133:18280-18288, incorporated herein by reference. In this technology, a short anchor region of a peptide capture molecule is designed that is specific for the protein to be bound, and then additional scaffolding regions are added to augment the anchor portion. While this method has been applied to proteins, it may also be extended to other analytes such as nucleic acids.

In the case of RNA, an amplification reaction using appropriate primers may be done quantitatively, and the amount of amplified RNA can then be determined with an appropriate probe with a detectable label. The probe may be an oligonucleotide including oligos with nonnative linkages such as phosphothiolate or phosphoramidate, or a peptide nucleic acid (PNA). Nonnative bases may also be included. Thus, "a reagent for the detection" of the marker refers specifically to the reagent in an assay for the concentration of the marker which reagent is specific for the marker, and additional reagents are sometimes or often needed in order to quantitate the results. The panels may be configured to measure more than one type of marker simultaneously, i.e., both miRNA and mRNA, both mRNA and protein, both mRNA and protein or all three simultaneously.

The levels of various markers in a sample can be measured individually using standard techniques well known in the art. The concentrations of specific proteins can be measured using methods such as Western blot, enzyme-linked immunosorbent assay (ELISA), radioimmunoassay (RIA), or mass spectrometry. For example, the concentration of a specific protein can be measured with ELISA, where one antibody specific to the targeted protein is immobilized on a solid surface. The sample with an unknown amount of protein of interest is exposed to the immobilized antibody and then a detection antibody is added to form a complex with the protein of interest. A secondary antibody reacts to the detection antibody that is linked to an enzyme through bioconjugation may then be added. Enzymatic substrate is introduced to produce a visible signal which reflects the concentration of protein of interest in the sample.

The concentration of specific proteins can also be measured by various mass spectrometry methods, such as the highly sensitive selected reaction monitoring (SRM) method. To quantify the concentrations of specific proteins using SRM, the levels of endogenous peptides derived from proteins of interest are determined by comparing their peak intensities with known concentrations of spiked-in synthetic heavy-isotopically labeled (e.g., D, $^{13}$C, or $^{15}$N) corresponding peptides. SRM technology is highly sensitive and allows the measurement of multiple proteins in the sample simultaneously.

Specific RNA levels can also be measured using general molecular biology techniques commonly known in the art such as Northern blot, quantitative reverse transcription polymerase chain reaction (qRT-PCR), next-generation sequencing or microarray.

The Northern blot may be used to measure gene expression level, and a denaturing gel is used to separate RNA by size. The bands are transferred to a solid matrix, and specific RNA molecules are detected with labeled probes complementary to the target RNA sequence. The probe can be labeled with radioisotope, florescent or ColorMatrix™ dye. qRT-PCR is a more sensitive and efficient procedure detect specific messenger RNA or microRNA. The RNA sample is first reverse transcribed, the target sequences can then be amplified using thermostable DNA polymerase. The concentration of a particular RNA sequence in a sample can be determined by examining the amount of amplified products. Microarray technology allows simultaneous measurement of the concentrations of multiple RNA species. The oligonucleotides complementary to specific RNA sequences are immobilized on solid support. The RNA in the sample is labeled with ColorMatrix™ or florescent dye. After subsequent hybridization of the labeled material to the solid support, the intensities of fluorescent for ColorMatrix™ dye remaining on the solid support determines the concentrations of specific RNA sequences in the samples.

The concentration of specific RNA species can also be determined by NanoString™ nCounter™ system which provides direct digital readout of the number of RNA molecules in the sample without the use of amplification. NanoString™ technology involves mixing the RNA sample with pairs of capture and reporter probes, tailored to each RNA sequence of interest. After hybridization and washing away excess probes, probe-bound target nucleic acids are stretched on a surface and scanned to detect fluorescent-barcodes of the reporter probes. This allows for up to 1000-plex measurement with high sensitivity and without amplification bias.

The concentrations of different types of molecular markers, such as proteins, mRNAs and miRNAs in a sample can also be measured simultaneously, on the same platform, using multiple types of technologies such as electrochemical biosensor array described by Mohan, et al. (*PLoS ONE* (_____) 6(10): e26846. doi:10.1371), or by surface plasma resonance or by NanoString™ nCounter™. Using NanoString™ nCounter™, for example, one can concurrently quantify the concentrations of the captured mRNA, miRNA, and proteins from a single sample of biological fluids. For this method, the RNA is captured using the standard NanoString™ nCounter™ protocols. The proteins are captured and isolated using DNA oligo tagged antibodies targeted for specific protein biomarkers of interest. The DNA oligo tags are isolated from the antibody-protein complexes and their concentrations are directly associated with the concentrations of the targeted protein biomarkers. From then on the DNA oligos are then treated in the same way as the isolated RNA. The captured mRNA, miRNA and DNA oligos can be mixed into a single tube and run through the NanoString™ nCounter™ prep station and digital analyzer together. The simultaneous measurement of RNA and protein biomarkers is not specific to the NanoString™ systems. Technologies such as electrochemical biosensor arrays, surface plasma resonance and other targeted capture assays can be utilized to quantify molecular markers simultaneously by measuring changes in electro-current, light absorption, fluorescence, or enzymatic substrates reactions.

The subjects of the assay are typically human but also include animal models for this disorder, such as rats, mice and non-human primates. In the event it is determined that the subject has PTSD, appropriate treatment is employed. Such treatment may include counseling, administering medications, physical therapy and combinations thereof.

Measures of the validity of an assay include sensitivity, specificity and area under the curve (AUC). Sensitivity is defined as the number of positives detected divided by the number of samples that were actually positive, according to an independent diagnosis. Specificity is defined as the number of samples that were assessed as negative divided by the number of samples that were in fact negative, according to an independent diagnosis. Thus, the sensitivity is a measure of success in identifying subjects who indeed have PTSD and specificity is a measure of the ability accurately to identify subjects who do not have PTSD.

The AUC reflects the area under the ROC curve for evaluating how well a parameter can distinguish between two groups. The true positive rate (Sensitivity, Y-axis) is plotted as a function of the false positive rate (100-Specificity, X-axis). Each point on the ROC curve represents a sensitivity/specificity pair corresponding to a particular decision or cutoff threshold. Thus the AUC is a measure of how well a parameter can distinguish between two groups, the higher the better. Ideally, a marker with perfect discrimination has a ROC curve that passes through the upper left corner (100% sensitivity, 100% specificity). Stated another way, the ROC curve determines the optimal cutoff for decision-making and the sensitivity/specificity depends on this cutoff. The AUC represents the probability that a classifier will rank a randomly chosen positive case higher than a randomly chosen negative one. AUC has been used as a performance measure of a model classifier.

In detail, the invention is directed to a panel for determining the probability of the presence or absence of post-traumatic stress disorder (PTSD) in a subject wherein said panel contains detection reagents for at least two microRNA selected from the group consisting of hsa-let-7a, hsa-let-7a*, hsa-miR-16, hsa-miR-33b, hsa-miR-146a, hsa-miR-185, hsa-miR-185*, hsa-miR-188-5p, hsa-miR-188-3p, hsa-miR-210, hsa-miR-505, hsa-miR-551, hsa-miR-598 and hsa-miR-663.

In one embodiment, said at least one detection reagent is for microRNA selected from hsa-let-7a*, hsa-miR-16, hsa-miR-33b, hsa-miR-185*, hsa-miR-210, hsa-miR-505, hsa-miR-551, and hsa-miR-663.

The invention is also directed to a panel for determining the probability of the presence or absence of PTSD in a subject wherein said panel contains detection reagents for at least two mRNA selected from the group consisting of HGD, RGS18, ND1, NT5C3, IGF2BP3, NEXN, HEXM2, DAPP1, SAV1, ID4, CXCR5, HS3ST1, CD72, TLR10, BANK1, MS4A1, FCRLA, CD79B, PPAPDC1B, TLC1A, KCNG1, FCRL1, FCRL2, BCOR, TC2N, LYPLAL1, RPA1, HMBOX1, RAMP1, FCGR1B, ADM, PRDM1, B4GALT5, MXRA7, TXNDC5, IGJ and LOC729451.

In one embodiment, said at least one detection reagent is for mRNA selected from RGS18, HGD, FCGR1B, ADM, PRDM1, B4GALT5, MXRA7, TXNDC5 and IGJ.

The invention is also directed to a panel for determining the probability of the presence or absence of PTSD in a subject wherein said panel contains detection reagents for at least two proteins selected from the group consisting of ANK3, APOD, BSN, CNP, CACNA1B, CNTN1, CNTN2, CRH, DCLK1, ELAVL3, ENC1, FSD1, FOXG1, GNAO1, GRIA1, GRIA2, GRIA3, GRIN1, GRM7, KCNC1, LGI1, LRRTM4, MAG, MAP3K12, MBP, NAP1L5, NCAM2, OLFM1, OLFM3, PRKAR1B, RASGRF1, RPH3A, SCG3, SNAP25, SST, STMN2, SYN1 and UCHL1.

In one embodiment, said at least one detection reagent is for the protein PRKAR1B or GRM7.

In one embodiment, the reagents of the panels are coupled to a solid substrate.

In another embodiment, the invention concerns a panel for determining the probability of the presence or absence of PTSD in a subject wherein said panel contains detection reagents for at least one microRNA and at least one mRNA; or
at least one microRNA and at least one protein; or
at least one mRNA and at least one protein; or
at least one microRNA and at least one mRNA and at least one protein.

One embodiment of the panel is that wherein the microRNA is selected from the group consisting of hsa-let-7a, hsa-let-7a*, hsa-miR-16, hsa-miR-33b, hsa-miR-146a, hsa-miR-185, hsa-miR-185*, hsa-miR-188-5p, hsa-miR-188-3p, hsa-miR-210, hsa-miR-505, hsa-miR-551, hsa-miR-598 and hsa-miR-663, and/or said mRNA is selected from the group consisting of HGD, RGS18, ND1, NT5C3, IGF2BP3, NEXN, HEXM2, DAPP1, SAV1, ID4, CXCR5, HS3ST1, CD72, TLR10, BANK1, MS4A1, FCRLA, CD79B, PPAPDC1B, TLC1A, KCNG1, FCRL1, FCRL2, BCOR, TC2N, LYPLAL1, RPA1, HMBOX1, RAMP1, FCGR1B, ADM, PRDM1, B4GALT5, MXRA7, TXNDC5, IGJ and LOC729451, and/or said protein is selected from the group consisting of ANK3, APOD, BSN, CNP, CACNA1B, CNTN1, CNTN2, CRH, DCLK1, ELAVL3, ENC1, FSID1, FOXG1, GNAO1, GRIA1, GRIA2, GRIA3, GRIN1, GRM7, KCNC1, LGI1, LRRTM4, MAG, MAP3K12, MBP, NAP1L5, NCAM2, OLFM1, OLFM3, PRKAR1B, RASGRF1, RPH3A, SCG3, SNAP25, SST, STMN2, SYN1 and UCHL1.

The invention also includes kits for determining the probability of the presence or absence of PTSD in a subject which comprises any of the panels described above and additional reagents for determining the level of said miRNA and/or mRNA and/or protein.

The invention further includes a method to evaluate the probability that a subject is afflicted with Posttraumatic Stress Disorder (PTSD), which method comprises:

assessing the level of at least one specific microRNA (miRNA) and/or of at least one specific messenger RNA (mRNA) and/or of at least one specific protein in a sample of cells and/or fluid from said subject and comparing the level of said at least one microRNA and/or mRNA and/or protein with the level associated with corresponding cells and/or fluid from control subjects who are free of PTSD, wherein a difference in the level of said one or more microRNA and/or mRNA and/or protein in said test subject as compared to control subjects indicates a probability that said subject is afflicted with PTSD.

In these methods, the levels of at least 2, 3, 4, 5 or 7 of said miRNA and/or said mRNA and/or said proteins are measured and compared.

Also in these methods, a single method simultaneously determines combinations or subcombinations of said miRNA, said mRNA and said protein levels.

In these methods, at least one said specific miRNA is selected from the group consisting of hsa-let-7a, hsa-let-7a*, hsa-miR-16, hsa-miR-33b, hsa-miR-146a, hsa-miR-185, hsa-miR-185*, hsa-miR-188-5p, hsa-miR-188-3p, hsa-miR-210, hsa-miR-505, hsa-miR-551, hsa-miR-598 and hsa-miR-663, and/or at least one said specific mRNA is selected from the group consisting of HGD, RGS18, ND1, NT5C3, IGF2BP3, NEXN, HEXM2, DAPP1, SAV1, ID4, CXCR5, HS3ST1, CD72, TLR10, BANK1, MS4A1, FCRLA, CD79B, PPAPDC1B, TLC1A, KCNG1, FCRL1, FCRL2, BCOR, TC2N, LYPLAL1, RPA1, HMBOX1, RAMP1, FCGR1B, ADM, PRDM1, B4GALT5, MXRA7, TXNDC5, IGJ and LOC729451, and/or at least one said specific protein is selected from the group consisting of ANK3, APOD, BSN, CNP, CACNA1B, CNTN1, CNTN2, CRH, DCLK1, ELAVL3, ENC1, FSD1, FOXG1, GNAO1, GRIA1, GRIA2, GRIA3, GRIN1, GRM7, KCNC1, LGI1, LRRTM4, MAG, MAP3K12, MBP, NAP1L5, NCAM2, OLFM1, OLFM3, PRKAR1B, RASGRF1, RPH3A, SCG3, SNAP25, SST, STMN2, SYN1 and UCHL1.

In one embodiment of these methods, at least one said specific miRNA is selected from the group consisting of hsa-let-7a, hsa-let-7a*, hsa-miR-16, hsa-miR-33b, hsa-miR-146a, hsa-miR-185, hsa-miR-185*, hsa-miR-188-5p, hsa-miR-188-3p, hsa-miR-210, hsa-miR-505, hsa-miR-551, hsa-miR-598 and hsa-miR-663, and at least one said specific mRNA is selected from the group consisting of HGD, RGS18, ND1, NT5C3, IGF2BP3, NEXN, HEXM2, DAPP1, SAV1, ID4, CXCR5, HS3ST1, CD72, TLR10, BANK1, MS4A1, FCRLA, CD79B, PPAPDC1B, TLC1A, KCNG1, FCRL1, FCRL2, BCOR, TC2N, LYPLAL1, RPA1, HMBOX1, RAMP1, FCGR1B, ADM, PRDM1, B4GALT5, MXRA7, TXNDC5, IGJ and LOC729451.

In another embodiment of these methods, at least one said specific miRNA is selected from the group consisting of hsa-let-7a, hsa-let-7a*, hsa-miR-16, hsa-miR-33b, hsa-miR-146a, hsa-miR-185, hsa-miR-185*, hsa-miR-188-5p, hsa-miR-188-3p, hsa-miR-210, hsa-miR-505, hsa-miR-551, hsa-miR-598 and hsa-miR-663, and at least one said specific protein is selected from the group consisting of ANK3, APOD, BSN, CNP, CACNA1B, CNTN1, CNTN2, CRH, DCLK1, ELAVL3, ENC1, FSD1, FOXG1, GNAO1, GRIA1, GRIA2, GRIA3, GRIN1, GRM7, KCNC1, LGI1, LRRTM4, MAG, MAP3K12, MBP, NAP1L5, NCAM2, OLFM1, OLFM3, PRKAR1B, RASGRF1, RPH3A, SCG3, SNAP25, SST, STMN2, SYN1 and UCHL1.

In another embodiment of these methods, at least one said specific mRNA is selected from the group consisting of HGD, RGS18, ND1, NT5C3, IGF2BP3, NEXN, HEXM2, DAPP1, SAV1, ID4, CXCR5, HS3ST1, CD72, TLR10, BANK1, MS4A1, FCRLA, CD79B, PPAPDC1B, TLC1A, KCNG1, FCRL1, FCRL2, BCOR, TC2N, LYPLAL1, RPA1, HMBOX1, RAMP1, FCGR1B, ADM, PRDM1, B4GALT5, MXRA7, TXNDC5, IGJ and LOC729451, and at least one said specific protein is selected from the group consisting of ANK3, APOD, BSN, CNP, CACNA1B, CNTN1, CNTN2, CRH, DCLK1, ELAVL3, ENC1, FSD1, FOXG1, GNAO1, GRIA1, GRIA2, GRIA3, GRIN1, GRM7, KCNC1, LGI1, LRRTM4, MAG, MAP3K12, MBP, NAP1L5, NCAM2, OLFM1, OLFM3, PRKAR1B, RASGRF1, RPH3A, SCG3, SNAP25, SST, STMN2, SYN1 and UCHL1.

In another embodiment of these methods, at least one said specific miRNA is selected from the group consisting of hsa-let-7a, hsa-let-7a*, hsa-miR-16, hsa-miR-33b, hsa-miR- 146a, hsa-miR-185, hsa-miR-185*, hsa-miR-188-5p, hsa-miR-188-3p, hsa-miR-210, hsa-miR-505, hsa-miR-551, hsa-miR-598 and hsa-miR-663, and at least one said specific mRNA is selected from the group consisting of HGD, RGS18, ND1, NT5C3, IGF2BP3, NEXN, HEXM2, DAPP1, SAV1, ID4, CXCR5, HS3ST1, CD72, TLR10, BANK1, MS4A1, FCRLA, CD79B, PPAPDC1B, TLC1A, KCNG1, FCRL1, FCRL2, BCOR, TC2N, LYPLAL1, RPA1, HMBOX1, RAMP1, FCGR1B, ADM, PRDM1, B4GALT5, MXRA7, TXNDC5, IGJ and LOC729451, and at least one said specific protein is selected from the group consisting of ANK3, APOD, BSN, CNP, CACNA1B, CNTN1, CNTN2, CRH, DCLK1, ELAVL3, ENC1, FSD1, FOXG1, GNAO1, GRIA1, GRIA2, GRIA3, GRIN1, GRM7, KCNC1, LGI1, LRRTM4, MAG, MAP3K12, MBP, NAP1L5, NCAM2, OLFM1, OLFM3, PRKAR1B, RAS-GRF1, RPH3A, SCG3, SNAP25, SST, STMN2, SYN1 and UCHL1.

In another embodiment of these methods, the method to evaluate the probability that a test subject is afflicted with Posttraumatic Stress Disorder (PTSD) comprises:

assessing the level of the protein PRKAR1B in a sample from said test subject and comparing said level of said PRKAR1B protein with the level of PRKAR1B protein associated with corresponding samples from control subjects who are free of PTSD, and wherein a difference in the level of said PRKAR1B protein in said test subject as compared to control subjects indicates a probability that said test subject is afflicted with PTSD, and/or assessing the level of mRNA representing expression of RGS18 in a sample from said test subject, and comparing said level of said RGS18 mRNA with the level of RGS18 mRNA associated with corresponding samples from control subjects who are free of PTSD, and wherein a difference in the level of said RGS18 in said test subject as compared to control subjects indicates a probability that said test subject is afflicted with PTSD.

In one embodiment, the method further includes assessing the level of at least one microRNA (miRNA) in a sample from the test subject and comparing said level with the level of said miRNA associated with corresponding samples from control subjects who are free of PTSD, wherein a difference in the level of said PRKAR1B protein and/or RGS18 mRNA and said at least one miRNA in said test subject as compared to control subjects indicates a probability that said test subject is afflicted with PTSD.

In another embodiment of these methods, at least one miRNA is selected from the group consisting of hsa-let-7a, hsa-let-7a*, hsa-miR-16, hsa-miR-33b, hsa-miR-146a, hsa-miR-185, hsa-miR-185*, hsa-miR-188-5p, hsa-miR-188-3p, hsa-miR-210, hsa-miR-505, hsa-miR-551, hsa-miR-598 and hsa-miR-663.

In another embodiment of these methods, the levels of 1-7 additional proteins are assessed, and/or wherein the levels of 1-7 additional mRNAs are assessed, and/or wherein the levels of 1-7 miRNAs are assessed.

In particular, one embodiment of panels useful in the method of the invention consists of 5 members, i.e., reagents for detection of:
PKA1B, miR-1207-5p, miR-16, miR-210 and miR-33b.

Another panel consists of 7 members, i.e., reagents for detection of: PKA1B, let-7a*, miR-16, miR-185*, miR-210, miR-33b and miR-505.

In another embodiment, the panel useful in the invention consists of 11 members, i.e., reagents for detection of: PKA1B, let-7a*, miR-146a, miR-16, miR-185*, miR-210, miR-33b, miR-451, miR-505, miR-551 and miR-663.

The following examples are offered to illustrate but not to limit the invention.

Example 1

Determination of MicroRNA Markers for PTSD

Blood plasma from 31 individuals including 14 PTSD positive and 17 PTSD negative controls was assayed using qRT-PCR for content of microRNAs. An initial screen using microRNA PCR panels (Exiqon, Mass., USA, Prod. #203607) wherein 742 microRNAs were assessed resulted in patterns wherein 20 microRNAs were differentially expressed in patients with PTSD. FIG. 1 shows the expression patterns obtained.

Using these data, blood plasma from 69 individuals different from those whose microRNA levels were as shown in FIG. 1 was assessed using qRT-PCR. Thirty-six of these individuals were diagnosed as without PTSD and 33 were diagnosed as afflicted with this disorder. Table 1 shows the sensitivity and specificity of assays conducted using each of these markers individually.

TABLE 1

List of Circulating MicroRNAs for PTSD Diagnosis

| microRNA | Sensitivity | Specificity | AUC* | Median Fold Change | P-value |
| --- | --- | --- | --- | --- | --- |
| miR-33b | 69.7 | 75 | 0.756 | 1.84 | 6.28E−5 |
| miR-210 | 66.7 | 80.8 | 0.723 | 1.46 | 2.12E−4 |
| miR-185* | 64.3 | 83.9 | 0.745 | 2.52 | 6.56E−7 |
| miR-505 | 68.7 | 80.6 | 0.754 | 1.19 | 1.64E−4 |
| miR-16 | 66.7 | 83.3 | 0.721 | 1.41 | 4.75E−4 |
| miR-663 | 75.8 | 83.8 | 0.883 | 2.13 | 6.61E−7 |
| miR-146a | 53.1 | 94.4 | 0.792 | 3.43 | 1.00E−02 |
| miR-551 | 69.7 | 75.8 | 0.737 | 1.58 | 8.15E−4 |
| let-7a* | 62.5 | 86.1 | 0.725 | 1.85 | 1.14E−3 |

*AUC (Area Under Curve).

As shown, reasonably satisfactory sensitivity and specificities were obtained even with individual markers.

Example 2

Identification of Messenger RNA Markers for PTSD

Figure 2:
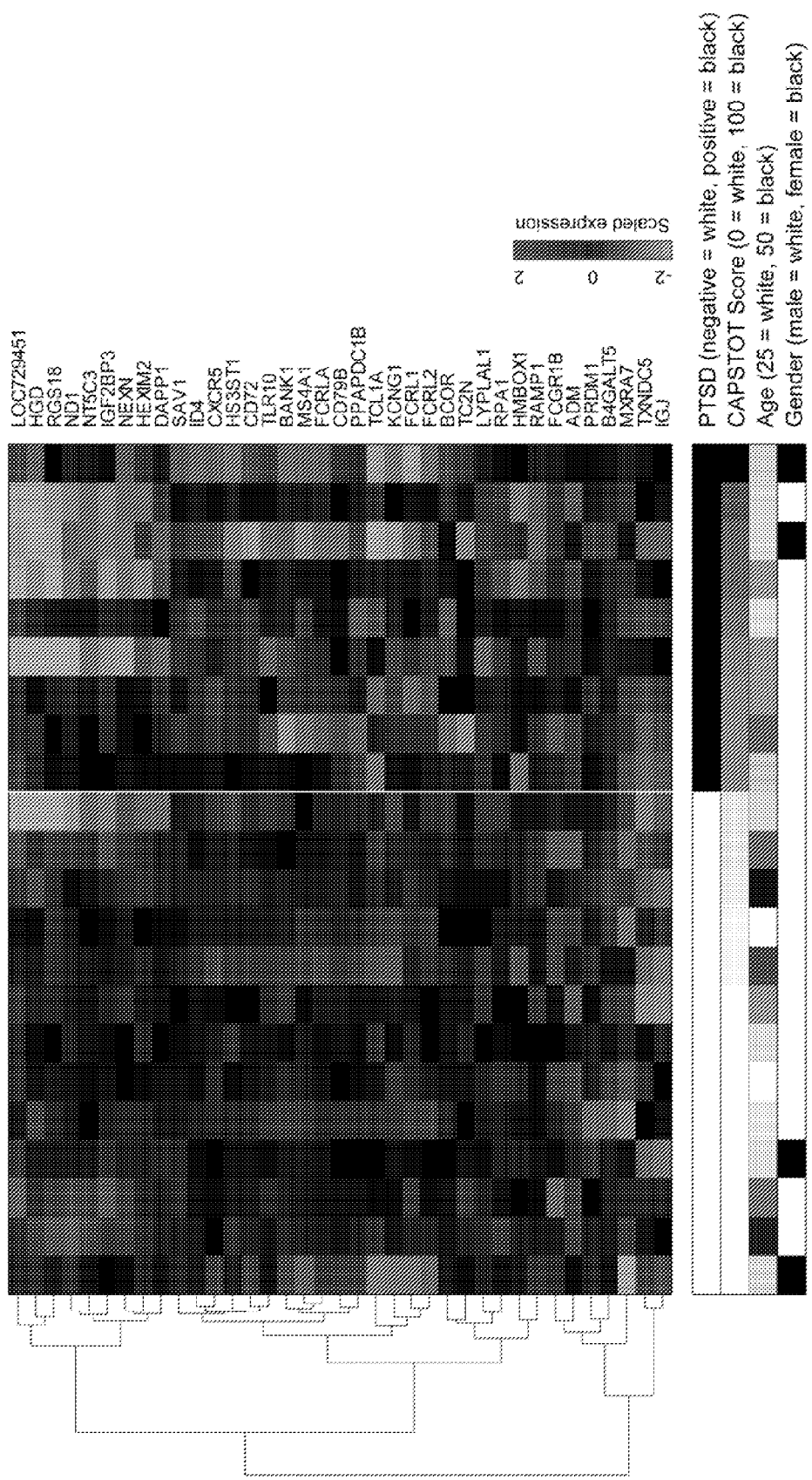
FIG. 2 shows the comparative expression levels measured as mRNA in human peripheral blood mononuclear cells (PBMC) separating PTSD positives from PTSD negatives.

Twenty-two peripheral blood mononuclear cell (PBMC) samples that included 9 PTSD positive and 13 PTSD negative individuals by independent diagnosis were assessed for levels or messenger RNA using whole genome microarrays supplied by Agilent 8×60K Microarray containing 56K genes (Agilent, Calif., USA, Product #G4852A). Thirty-seven differentially expressing genes in patients with PTSD were found. The expression pattern of these is shown in FIG. 2. Using these data, blood PBMC from 107 individuals different from those whose mRNA levels were as shown in FIG. 2 was assessed using qRT-PCR. Sixty-one of these individuals were diagnosed as without PTSD and 46 were diagnosed as afflicted with this disorder. Table 2 shows the sensitivity and specificity of assays conducted using two of these markers, RGS18 (regulator of G-protein signaling 18) and HGD (homogentisate 1,2-dioxygenase), individually.

The levels of mRNA are lower in individuals suffered with PTSD than in normal as indicated by the negative fold changes in Table 2.

TABLE 2

List of blood mRNAs for PTSD Diagnosis

| mRNA | Sensitivity | Specificity | AUC | Median Fold Change | P-value |
|---|---|---|---|---|---|
| RGS18 | 78.3 | 78.7 | 0.803 | −1.65 | 1.27E−6 |
| HGD | 66.7 | 82.5 | 0.733 | −1.04 | 7.17E−3 |

Figure 4:
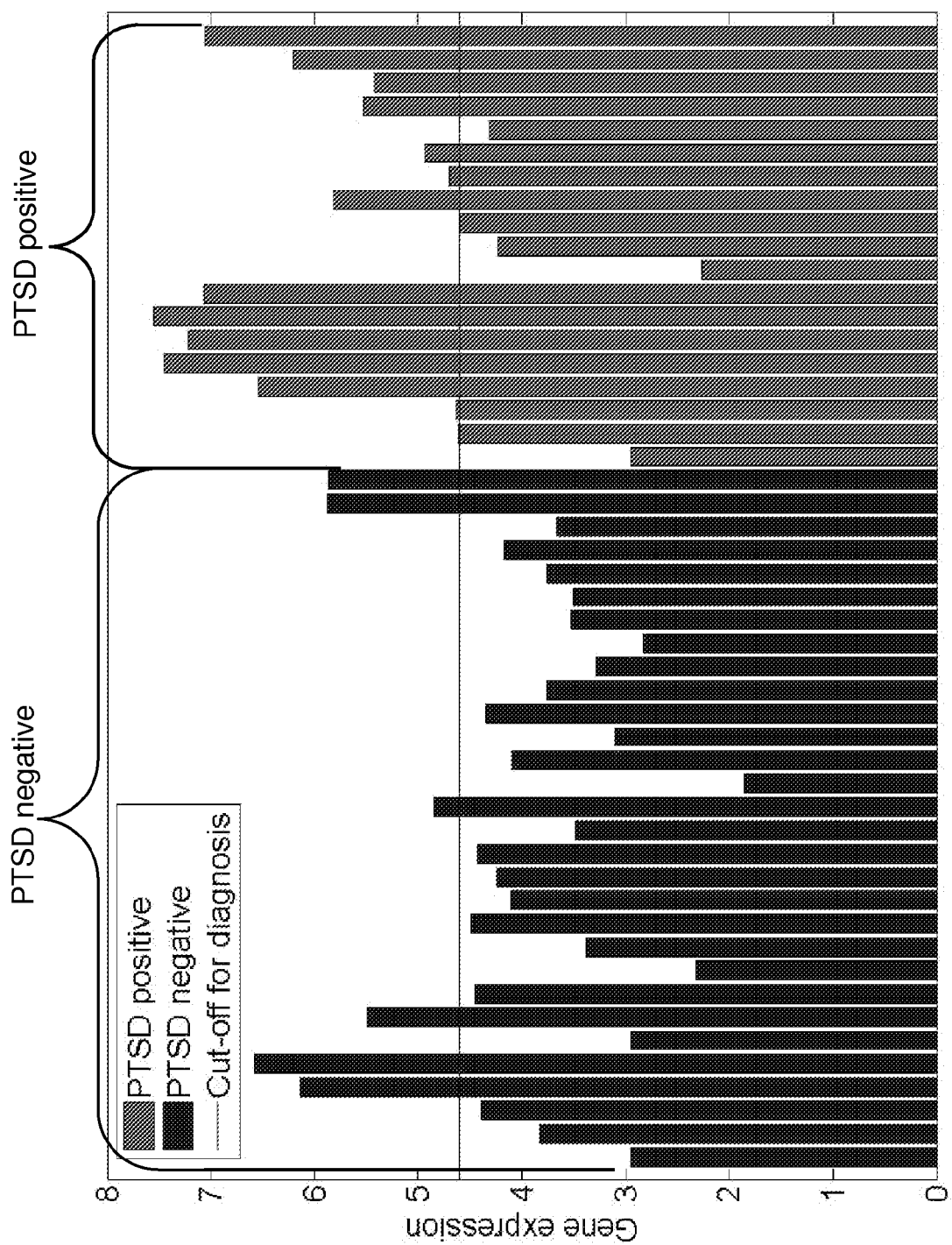
FIG. 4 shows the results from the using gene expression level for RGS18 as a classifier.

In another experiment, mRNA representing RGS18 was determined in blood samples of peripheral blood mononuclear cells (PBMC) from 49 human subjects. Nineteen of the subjects were PTSD positive and 30 were PTSD negative. Based on a cutoff value of 4.6010, the assay had a sensitivity of 0.7895, a specificity of 0.8, and an AUC of 0.7860. These results are shown in FIG. 4 where each bar represents the gene expression level for RGS18 for each sample. Among the PTSD negative samples, only six samples were misclassified as PTSD positive and among 19 PTSD positive samples, four samples were misclassified as PTSD negative.

Example 3

Comparison to Multivariate Analysis

Figure 5:
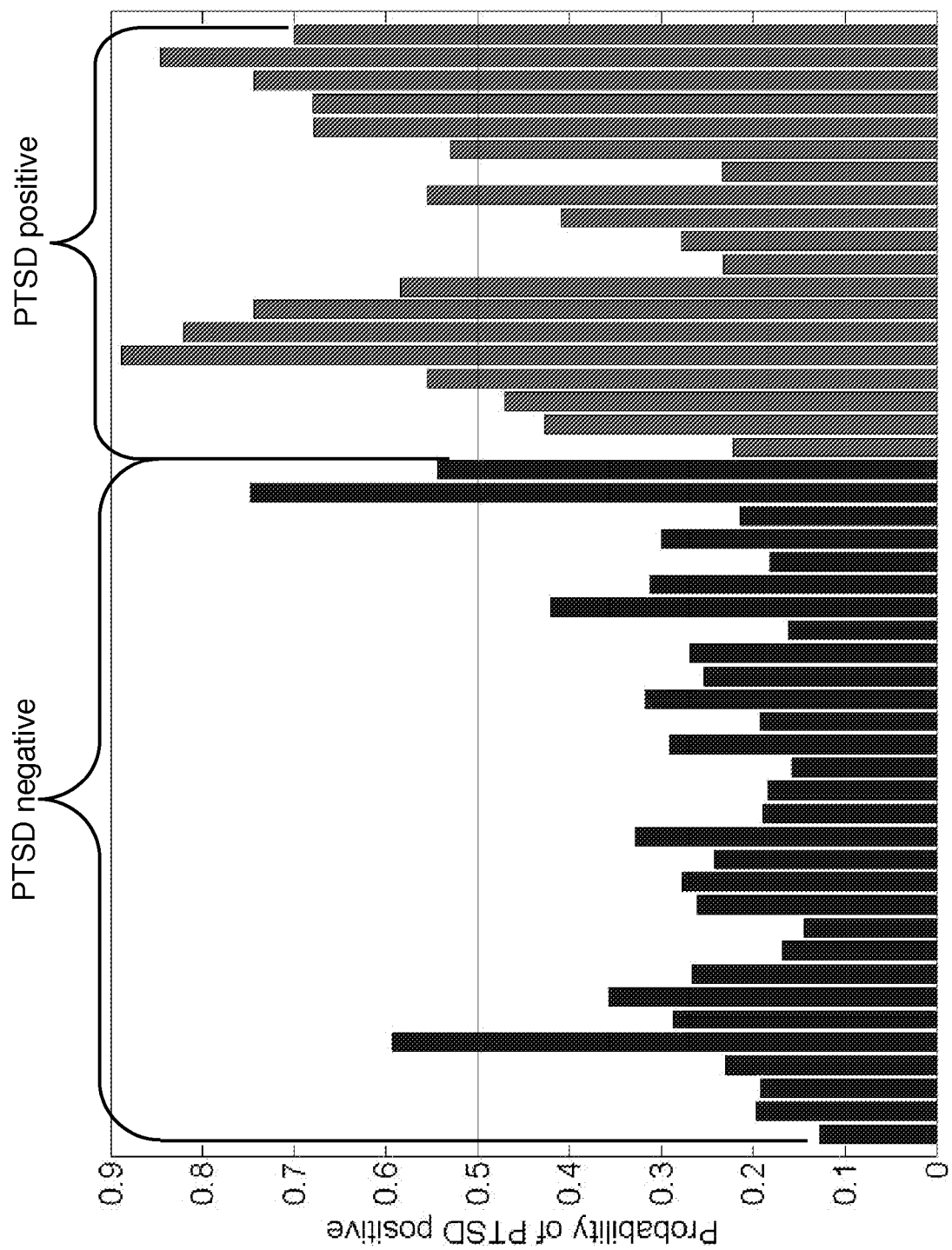
FIG. 5 shows the results from a multivariate model using the same subjects as FIG. 4.

For the same set of 49 samples as in Example 2, the measurements of 14 molecules (microRNAs, mRNAs and proteins) were available and a multivariate classifier using generalized linear logistic regression approach was constructed (among 14 molecules, 13 molecules were used for modeling). Since the model is a classifier, it tries to maximize the separability which makes PTSD negative samples have low probability of being PTSD positive and vice versa. The model produced output scores of samples representing the probability of being PTSD positive as shown in FIG. 5, which resulted in sensitivity=0.6316, specificity=0.9 and AUC=0.8474. Note that cut-off of the model is always 0.5 since the output scores represent probabilities (so, greater than 0.5 will be regarded as PTSD positive and vice versa). As shown in FIG. 5, only six of the PTSD negative samples were misclassified and four PTSD positive samples were misclassified.

Figure 6:
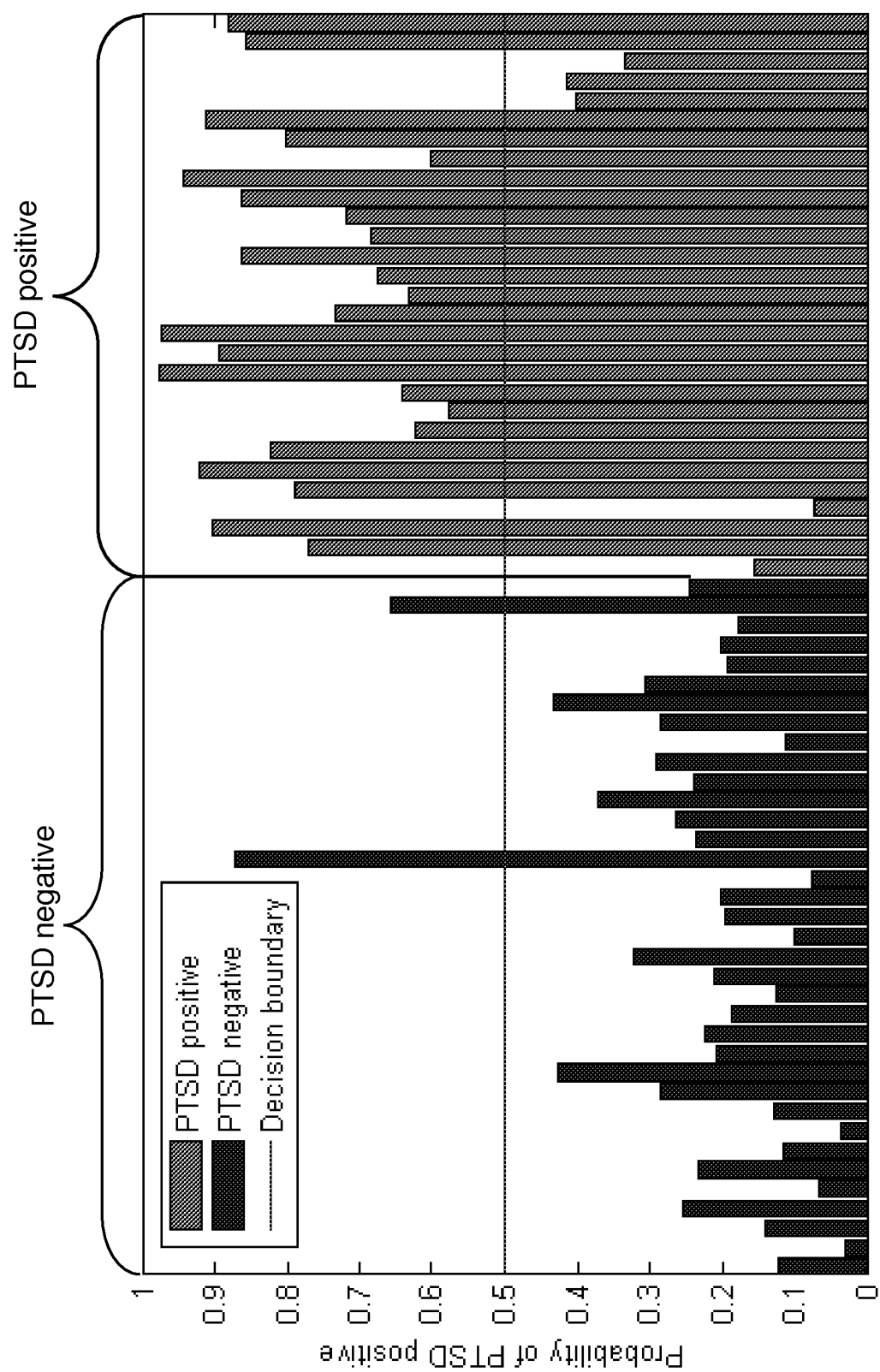
FIG. 6 shows the correlation of results with predictions from an additional multivariate model.

Comparing these results with those of Example 2, in terms of (optimal) sensitivity and specificity, the classifier with RGS18 looks better than the multivariate model. However FIG. 6 shows the variation of samples within the same group seems to be fairly high, which suggests the classifier might be sensitive to small amount of noise. On the other hand, in the multivariate model shown in FIG. 5, the output scores within the same group look more homogeneous as reflected by higher AUC value (0.8474). Although a model with high sensitivity, specificity and AUC is ideally preferred, in other cases, the selection of a model with higher AUC might be more preferred. In general, multivariate approach produces a model having higher AUC value than univariate classifiers.

Example 4

Protein Markers

Ninety-seven human plasma samples were analyzed of which 53 were PTSD positive and 44 were PTSD negative by independent diagnosis. Selected proteins were analyzed by Western blot. Differential concentrations or levels of two proteins, PRKAR1B (protein kinase, camp-dependent, regulatory, type I, beta) and GRAM7 (glutamate receptor, metabotropic 7) were shown to correlate with PTSD as shown in Table 3.

TABLE 3

List of Circulating Brain-Specific Protein for PTSD Diagnosis

| Blood Protein | Sensitivity | Specificity | AUC |
|---|---|---|---|
| PRKAR1B | 77.3 | 77.9 | 0.803 |
| GRAM7 | 56.1 | 67.6 | 0.733 |

Figure 3:
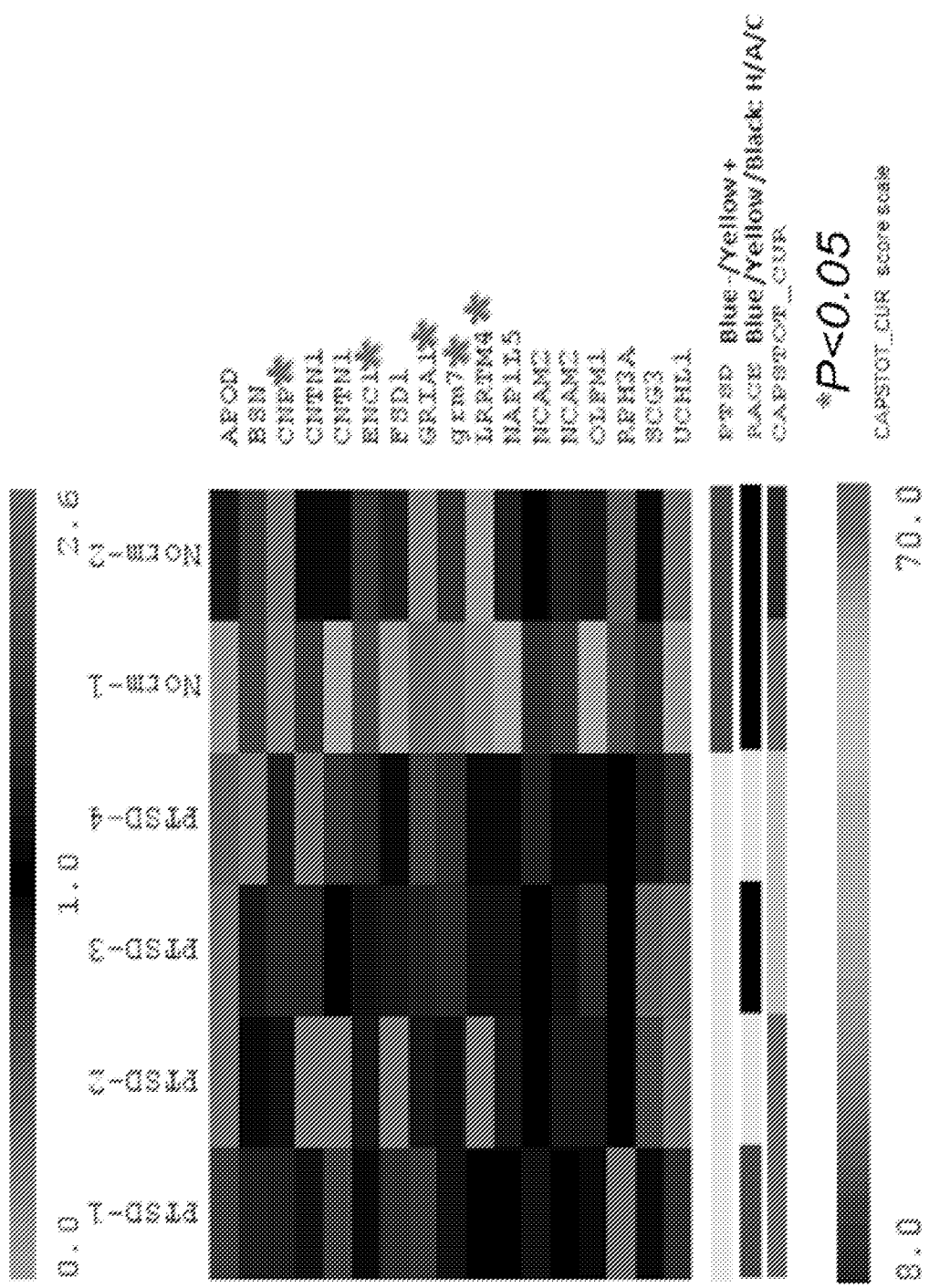
FIG. 3 shows a comparison of levels of various proteins in PTSD positive versus PTSD negative subjects.

Alternatively, the levels of various brain specific proteins in four PTSD positive and two PTSD negative samples were measured by mass spectrometry based measurement, SRM (single reaction monitor). Proteins that show different concentration levels between normal individuals and PTSD patients were found, examples of these proteins as shown in FIG. 3.

As PRKAR1B was found to be particularly favorable as a marker of PTSD according to Western blot, plasma concentrations of this protein in a PTSD animal model were measured also by Western blotting. The concentration of PRKAR1B showed a significant increase in plasma after the animal had been exposed to a stress condition as observed in human PTSD patient blood samples.

Alternatively, the change of global plasma proteome in PTSD was measured by quantitative proteomic technology. Four PTSD patient plasma samples and four control plasmas were labeled with one channel of 8-plex iTRAQ® (Isobaric tags for relative and absolute quantitation) reagent, respectively. The 8-plex iTRAQ® labeled peptides were then mixed together and fractionated to 24 fractions with Off-gel fractionator (pH 3-10). The peptide fractions were analyzed on a high-performance linear ion trap LTQ™-Orbitrap/Velos Hybrid mass spectrometer to generate high-resolution plasma proteome maps. After searching against human whole proteome sequence database, a total of 1,545 unique peptides which represent 245 distinct proteins (199 gene symbols) were identified with error rate <0.05. The intensities of reporter ions from 8-plex iTRAQ® labeling were also extracted, normalized and used as protein quantitation. About 180 proteins were observed and quantified in all 8 samples. Comparing the average protein concentration changes in each group, 31 proteins were identified to be significantly elevated in PTSD plasma (p-value of less than 0.01) and three proteins were suppressed in the PTSD samples (Table 4).

TABLE 4

List of Circulating Protein for PTSD Diagnosis

| Gene Symbol | Gene description | PTSD/Control Fold Changes |
|---|---|---|
| CFL1 | Cofilin-1 | 21.25 |
| YWHAZ | 14-3-3 protein zeta/delta | 15.77 |
| PDLIM1 | PDZ and LIM domain protein 1 | 12.49 |
| PFN1 | Profilin-1 | 15.61 |
| TPM4 | Isoform 1 of Tropomyosin alpha-4 chain | 7.64 |
| PPBP | Platelet basic protein | 10.19 |
| CMPK1 | Cytidine monophosphate (UMP-CMP) kinase 1 | 7.56 |

TABLE 4-continued

List of Circulating Protein for PTSD Diagnosis

| Gene Symbol | Gene description | PTSD/Control Fold Changes |
|---|---|---|
| PLEK | Pleckstrin | 5.98 |
| TPM3 | Tropomyosin alpha-3 chain | 5.98 |
| TAGLN2 | Transgelin-2 | 6.57 |
| ACTN1 | Alpha-actinin-1 | 6.50 |
| TLN1 | Talin-1 | 7.31 |
| ITGA2B | Integrin alpha-Iib | 5.78 |
| F13A1 | Coagulation factor XIII A chain | 4.82 |
| TPI1 | Triosephosphate isomerase | 4.77 |
| HSPA8 | Heat shock cognate 71 kDa protein | 4.35 |
| MIF | Macrophage migration inhibitory factor | 4.04 |
| THBS1 | Thrombospondin-1 | 5.14 |
| FERMT3 | Fermitin family homolog 3 | 4.30 |
| HSPC159 | Galectin-related protein | 3.99 |
| VCL | Vinculin | 3.64 |
| LBP | Lipopolysaccharide-binding protein | 2.80 |
| EIF4A1 | Eukaryotic initiation factor 4A-I | 2.66 |
| LDHB | L-lactate dehydrogenase B chain | 2.77 |
| GSTO1 | Glutathione S-transferase omega-1 | 2.77 |
| P4HB | Protein disulfide-isomerase | 2.47 |
| ALDOA | Fructose-bisphosphate aldolase A | 2.73 |
| CRP | C-reactive protein | 2.44 |
| PKM2 | Pyruvate kinase isozymes M1/M2 | 2.56 |
| SOD1 | Superoxide dismutase [Cu—Zn] | 2.11 |
| CYCS | Cytochrome c | 2.08 |
| DCD | Dermcidin | −2.48 |
| KRT10 | Keratin, type I cytoskeletal 10 | −2.44 |
| C7 | Complement component C7 | −3.60 |

Example 5

Multivariate Models

A multivariate model was constructed using combined measurements of multiple miRNAs and protein. A linear logistic regression model with Ridge parameter was applied to measurements of miR-33b, miR-210, miR-505, let-7a* and PRKAR1B protein across 65 samples. The model is according to Friedman, et al., *J. Stat. Software* (2010) 33:1-22. The model parameter was determined using the leave-one-out cross-validation, that is using a single measurement result from the sample as the validation data, and the remaining measurements (markers) as the training data. This is used to evaluate the performance of omitted marker. The method is well known in the art. The output from the model represents the probability of PTSD positive for each sample as shown in FIG. 6. As shown, of 36 PTSD negative samples, only two samples were misclassified as positive and among 29 PTSD positive samples, five samples were misclassified as negative.

Thus, the combined assay (panel) has a sensitivity of 82.8 and a specificity of 94.4.

Example 6

Various Classifiers Among 100 Samples

Micro RNAs (miRNAs)

Among 100 samples, seven miRNAs were completely measured in 86 samples. The results are shown in Table 5.

TABLE 5

|  | Sensitivity | Specificity | AUC |
|---|---|---|---|
| miR-33b | 0.767442 | 0.627907 | 0.699838 |
| miR-210 | 0.651163 | 0.72093 | 0.693889 |
| miR-505 | 0.604651 | 0.697674 | 0.680638 |
| miR-16 | 0.604651 | 0.72093 | 0.633856 |
| let-7a* | 0.465116 | 0.813953 | 0.630341 |
| miR-185* | 0.651163 | 0.697674 | 0.685235 |
| miR-663 | 0.488372 | 0.744186 | 0.613845 |
| Model with 6 miRNAs | 0.627907 | 0.744186 | 0.750135 |

Messenger RNAs (mRNAs)

Among 100 samples, five mRNAs were flawlessly measured in 65 samples. The results are shown in Table 6.

TABLE 6

|  | Sensitivity | Specificity | AUC |
|---|---|---|---|
| RGS18 | 0.782609 | 0.809524 | 0.809524 |
| NEXN | 0.695652 | 0.833333 | 0.792961 |
| NT5C3 | 0.782609 | 0.738095 | 0.798137 |
| ADM | 0.304348 | 0.833333 | 0.589027 |
| HGD | 0.826087 | 0.785714 | 0.795031 |
| Model with 5 genes | 0.434783 | 0.928571 | 0.811594 |

Proteins

Among 100 samples, two proteins were measured in 85 samples. The results are shown in Table 7.

TABLE 7

|  | Sensitivity | Specificity | AUC |
|---|---|---|---|
| PKA1B | 0.682927 | 0.75 | 0.703991 |
| GRM7 | 0.512195 | 0.704545 | 0.570953 |
| Model with 1 protein | 0.560976 | 0.75 | 0.703991 |

Combination of microRNAs and mRNAs

Seven miRNAs and five mRNAs were completely measured in 56 samples. The results are shown in Table 8.

TABLE 8

|  | Sensitivity | Specificity | AUC |
|---|---|---|---|
| miR-33b | 0.714286 | 0.685714 | 0.721088 |
| miR-210 | 0.666667 | 0.8 | 0.757823 |
| miR-505 | 0.666667 | 0.742857 | 0.736735 |
| miR-16 | 0.52381 | 0.8 | 0.644898 |
| let-7a* | 0.47619 | 0.914286 | 0.67415 |
| miR-185* | 0.47619 | 0.942857 | 0.689796 |
| miR-663 | 0.666667 | 0.771429 | 0.703401 |
| RGS18 | 0.809524 | 0.8 | 0.795918 |
| NEXN | 0.714286 | 0.828571 | 0.77415 |
| NT5C3 | 0.809524 | 0.714286 | 0.798639 |
| ADM | 0.285714 | 0.885714 | 0.578231 |
| HGD | 0.809524 | 0.771429 | 0.778231 |
| Model with all | 0.571429 | 0.914286 | 0.840816 |

Combination of microRNAs and Proteins

Seven miRNAs and two proteins were completely measured in 73 samples. The results are shown in Table 9.

TABLE 9

|  | Sensitivity | Specificity | AUC |
|---|---|---|---|
| miR-33b | 0.7568 | 0.6389 | 0.7230 |
| miR-210 | 0.6757 | 0.7778 | 0.7305 |
| miR-505 | 0.4054 | 0.8889 | 0.6888 |
| miR-16 | 0.5946 | 0.8333 | 0.6787 |
| let-7a* | 0.4865 | 0.8333 | 0.6573 |
| miR-185* | 0.6486 | 0.7500 | 0.7042 |
| miR-663 | 0.5135 | 0.7500 | 0.6149 |
| PKA1B | 0.6757 | 0.7222 | 0.7005 |
| GRM7 | 0.5405 | 0.7222 | 0.5968 |
| Model (except miR-16) | 0.6486 | 0.7778 | 0.7928 |

Combination of mRNAs and Proteins

Five mRNAs and two proteins were completely measured in 56 samples. The results are shown in Table 10.

TABLE 10

|  | Sensitivity | Specificity | AUC |
|---|---|---|---|
| RGS18 | 0.7619 | 0.8000 | 0.7973 |
| NEXN | 0.7143 | 0.8000 | 0.7932 |
| NT5C3 | 0.7619 | 0.7714 | 0.7986 |
| ADM | 0.3333 | 0.8571 | 0.5646 |
| HGD | 0.8095 | 0.7429 | 0.7673 |
| PKA1B | 0.5714 | 0.7429 | 0.6068 |
| GRM7 | 0.5238 | 0.7143 | 0.5932 |
| Model with 3 genes and GRM7 | 0.4762 | 0.8857 | 0.8109 |

Combination of microRNAs, mRNAs and Proteins

All miRNAs, mRNAs and proteins were measured in 49 samples. The results are shown in Table 11.

TABLE 11

|  | Sensitivity | Specificity | AUC |
|---|---|---|---|
| miR-33b | 0.6842 | 0.6667 | 0.7035 |
| miR-210 | 0.6842 | 0.8333 | 0.7877 |
| miR-505 | 0.8421 | 0.5667 | 0.7447 |
| miR-16 | 0.4737 | 0.9000 | 0.6632 |
| let-7a* | 0.4737 | 0.9000 | 0.6693 |
| miR-185* | 0.5263 | 0.9333 | 0.7123 |
| miR-663 | 0.6842 | 0.8000 | 0.7228 |
| RGS18 | 0.7895 | 0.8000 | 0.7860 |
| NEXN | 0.7368 | 0.8000 | 0.7789 |
| NT5C3 | 0.7895 | 0.7333 | 0.7982 |
| ADM | 0.3158 | 0.8667 | 0.5667 |
| HGD | 0.7895 | 0.7333 | 0.7526 |

TABLE 11-continued

|  | Sensitivity | Specificity | AUC |
|---|---|---|---|
| PKA1B | 0.6842 | 0.6333 | 0.6281 |
| GRM7 | 0.5789 | 0.7000 | 0.6263 |
| Model (except miR-16) | 0.6316 | 0.9000 | 0.8474 |

Example 7 Performance of Panels Comprising Proteins and miRNA's in Kernel Fisher Discrimination Analysis Eighty-five participants, of whom 43 were PTSD-negative and 42 PTSD-positive provided samples that were tested with a panel of 11 members including reagents for detection of 10 miRNA's and one protein: PKA1B, let-7a*, miR-146a, miR-16, miR-185*, miR-210, miR-33b, miR-451, miR-505, miR-551 and miR-663. The results showed an AUC of 0.986, a sensitivity of 0.952, a specificity of 0.930 and an accuracy of 0.941.

An additional set of 92 subjects of whom 49 were PTSD-negative and 43 PTSD-positive were tested with a panel of seven members including reagents for detection of one protein and six miRNA's: PKA1B, let-7a*, miR-16, miR-185*, miR-210, miR-33b and miR-505. The results of this assay showed an AUC of 0.849, a sensitivity of 0.744, a specificity of 0.918 and an accuracy of 0.837.

An additional assay involving a panel of five members for detection of: PKA1B, miR-1207-5p, miR-16, miR-210 and miR-33b was tested on the same 85 subjects that were tested with the panel of 11 members directed above. The results of this assay showed an AUC of 0.895, a sensitivity of 0.810, a specificity of 0.884, and an accuracy of 0.847.

The invention claimed is:

1. A single panel for determining the probability of the presence or absence of Posttraumatic Stress Disorder (PTSD) in a test subject, wherein the single panel contains in an organized array on a single solid support, detection reagents selected from the group consisting of antibodies, aptamers, oligonucleotide probes and combinations thereof that detect at least nine miRNA markers of PTSD and at least one protein marker of PTSD, wherein the at least nine miRNA markers of PTSD are hsa-let-7a*, hsa-miR-16, hsa-miR-33b, hsa-miR-185*, hsa-miR-210, hsa-miR-505, hsa-miR-551, hsa-miR-146a and hsa-miR-663, and the at least one protein marker of PTSD is PRKAR1B.

2. A method to evaluate the probability that a test subject is afflicted with Posttraumatic Stress Disorder (PTSD), which method comprises:
    (a) contacting a biological sample obtained from the test subject with the single panel of claim 1; and
    (b) assessing the level of interaction between the detection reagents on the single panel of claim 1 and said biological sample, wherein the difference in the level of said interaction in said test subject as compared to a corresponding biological sample from a control subject indicates a probability that the test subject is afflicted with PTSD, wherein said control subject is a normal subject that is not afflicted with PTSD.

3. The single panel of claim 1 wherein the solid support is latex.

* * * * *